United States Patent
Hiejima (10) Patent No.: US 6,786,891 B2
(45) Date of Patent: Sep. 7, 2004

(54) INDWELLING NEEDLE

(75) Inventor: Katsuhiro Hiejima, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/442,210

(22) Filed: May 21, 2003

(65) Prior Publication Data

US 2003/0220612 A1 Nov. 27, 2003

(30) Foreign Application Priority Data

May 24, 2002 (JP) ........................................ 2002-149923

(51) Int. Cl.[7] .......................................... A61M 5/178
(52) U.S. Cl. ................................................ 604/164.01
(58) Field of Search ................................ 604/165, 177, 604/264, 164.01, 164.02, 164.04, 164.08, 164.09, 164.11, 165.01–165.04, 167.01–167.03, 524, 525, 526, 527, 256, 905

(56) References Cited

U.S. PATENT DOCUMENTS

| | | | |
|---|---|---|---|
| 4,177,809 A | | 12/1979 | Moorehead ............... 128/214.4 |
| 4,235,232 A | | 11/1980 | Spaven et al. ........... 128/214.4 |
| 4,366,817 A | * | 1/1983 | Thomas ....................... 604/174 |
| 4,445,893 A | * | 5/1984 | Bodicky ................. 604/165.04 |
| 5,102,401 A | * | 4/1992 | Lambert et al. ............ 604/264 |
| 5,163,913 A | | 11/1992 | Rantanen-Lee et al. ..... 604/177 |
| 5,226,899 A | * | 7/1993 | Lee et al. .................... 604/524 |
| 5,685,858 A | | 11/1997 | Kawand ...................... 604/171 |
| 5,797,882 A | * | 8/1998 | Purdy et al. ........... 604/164.09 |
| 5,993,436 A | * | 11/1999 | Kitou et al. ................. 604/531 |
| 6,210,396 B1 | * | 4/2001 | MacDonald et al. ........ 604/529 |
| 6,485,473 B1 | * | 11/2002 | Lynn .......................... 604/256 |

FOREIGN PATENT DOCUMENTS

| EP | 0 339 812 A2 | 11/1989 |
|---|---|---|
| WO | 01 12249 A1 | 2/2001 |

* cited by examiner

Primary Examiner—Manuel Mendez
(74) Attorney, Agent, or Firm—Kubovcik & Kubovcik (57) ABSTRACT

An indwelling needle of the present invention comprises a flexible cover needle, a fixing wing externally fitted and fixed on a distal end of the cover needle, a cover needle hub mounted on a proximal end of the cover needle, an inner needle which is removably inserted through the cover needle and the cover needle hub and the distal end of which projects forwards from the cover needle, and a protecting tube for preventing kink of the cover needle which is externally fitted between the fixing wing and the cover needle hub on the cover needle.

5 Claims, 11 Drawing Sheets

Fig. 12

INDWELLING NEEDLE

BACKGROUND OF THE INVENTION

The present invention relates to an indwelling needle which is used in infusion of a liquid medicine, blood and the like or in blood collection and the like by being stuck in a peripheral vein, under a skin, etc.

For infusion from a peripheral vein in the back of a hand, it is required to curve an infusion route. Therefore, an indwelling needle of a winged needle (with wings) type (PSV) is used. The indwelling needle of a winged needle type has a hollow needle and a fixing wing which is externally fitted and fixed on a distal end of the hollow needle and fixed on a skin.

In the foregoing indwelling needle, a hollow needle made of metal is mainly used. When such a hollow needle made of a metal is used, a blood vessel might be damaged with an edge of the hollow needle during indwelling of the needle in the blood vessel. Accordingly, there was a problem that the indwelling needle could not be used for administration of a liquid medicine over a long period of time or indwelling in a blood vessel over a long period of time.

In the case that an indwelling needle is used for administration of a liquid medicine over a long period of time or indwelling in a blood vessel over a long period of time, an indwelling needle was used which comprises a cover needle made of plastics, a fixing wing externally fitted and fixed on a distal end of the cover needle and an inner needle made of metal which is detachably inserted into the cover needle and whose distal end is projected forwards from the cover needle. In infusion, the inner needle and the cover needle are first stuck into a blood vessel of a patient, the inner needle is then drawn out from the cover needle and only the cover needle is indwelled in the blood vessel to perform infusion. However, since the cover needle made of plastic tends to kink, it is difficult for the cover needle to be curved for fixing on a patient's arm with tape or the like.

An indwelling needle solving such a problem has been proposed in U.S. Pat. Nos. 4,177,809 and 5,163,913 and has been commercialized by Nippon Becton Dickinson Company, Ltd. as Intima (trade mark). However, since the foregoing needle is complicated in structure and costly, it has not been widespread in Japan.

SUMMARY OF THE INVENTION

The present invention aims to provide an indwelling needle which, although a cover needle is made of plastics, does not kink so that a procedure of curving the cover needle to fix it on an arm or the like of a patient with a tape or the like for infusion is easily practiced. With the indwelling needle, infusion or blood collection from a peripheral vein in the back of a hand or the like is easily and satisfactorily conducted. Additionally, the indwelling needle is simple in structure and can be manufactured at low cost.

For attaining the foregoing aim, the present invention is characterized by an indwelling needle comprising (A) a flexible cover needle made of plastic, (B) a fixing wing externally fitted and fixed on a distal end of the cover needle, (C) a cover needle hub mounted on a proximal end of the cover needle, and (D) an inner needle which is removably inserted through the cover needle and the cover needle hub and the distal end of which projects forwards from the cover needle, with a kink preventing means for preventing kink of a portion of the cover needle between the fixing wing and the cover needle hub being provided on the cover needle.

The kink preventing means may be a protecting tube externally fitted on the cover needle or protecting members mounted around the cover needle and being spaced apart from each other.

In certain embodiments, the fixing wing may have a fixing means for releasably fixing the cover needle and the inner needle.

In certain embodiments, the fixing wing may comprise a holding tube externally fitted and fixed on the cover needle, a pair of wing parts projecting outwardly from the holding tube to the right and left sides, and a pair of connecting portions for connecting an upper surface or a lower surface of each wing part and the holding tube, and the fixing means may be a means for fixing the cover needle and the inner needle by bringing both of the wing parts relatively close to each other to press the holding tube and the cover needle via the respective connecting portions diametrically inward.

In certain embodiments, an inner needle hub is mounted on a proximal end of the inner needle, and an inner needle housing which is interposed between a proximal end of the cover needle hub and the inner needle hub, comprises (A) an inner tube in which the inner needle is inserted, (B) an outer tube which is externally fitted on the inner tube, and (C) a sleeve which is externally fitted on the inner tube, a distal end of which is fixed on the inner needle housing, a proximal end of which is externally fitted and fixed on a distal end of the inner needle hub, and which is housed between the inner tube and the outer tube in an axially folded state and is axially extended when the inner needle is removed from the cover needle and the cover needle hub to cover a portion of the inner needle which is situated on a more proximal side than the inner tube.

In some cases, the inner needle housing may include a pressing portion capable of pressing against an outer surface of the inner needle in a state that the inner needle 5 is slidable against the pressing portion, and capable of deforming diametrically inwards by its own resilient force to have an inner diameter which is smaller than an outer diameter of the inner needle after the inner needle is drawn out backwards from the pressing portion.

DESCRIPTION OF THE DRAWINGS

The indwelling needle of the present invention is described in detail below by referring to preferred embodiments shown in the appended drawings. However, the invention is not limited to these descriptions.

DETAILED DESCRIPTION OF THE INVENTION

Figure 1:
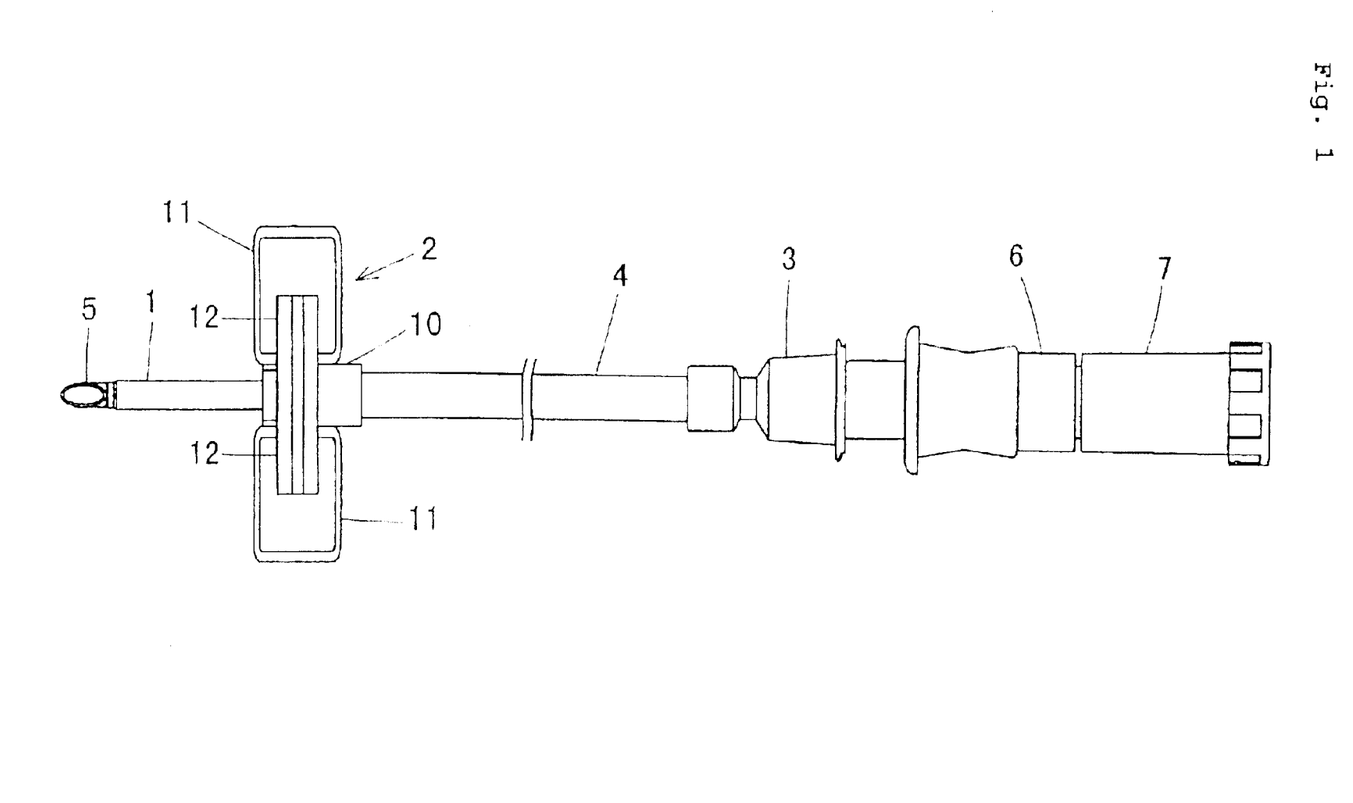
FIG. 1 is a plane view showing a first embodiment of the indwelling needle of the present invention.
Figure 2:
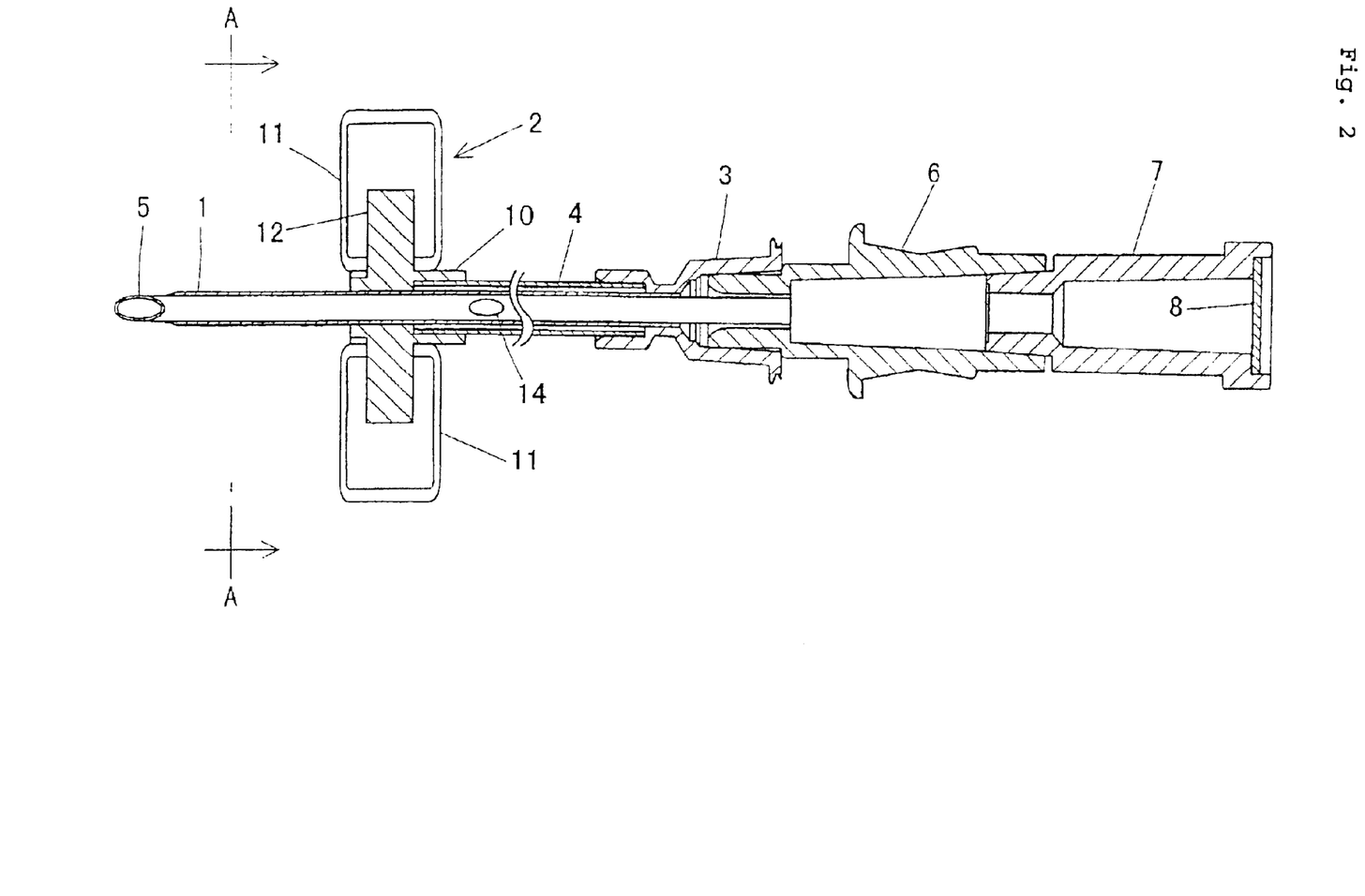
FIG. 2 is a sectional view of the indwelling needle disclosed in FIG. 1.
Figure 3:
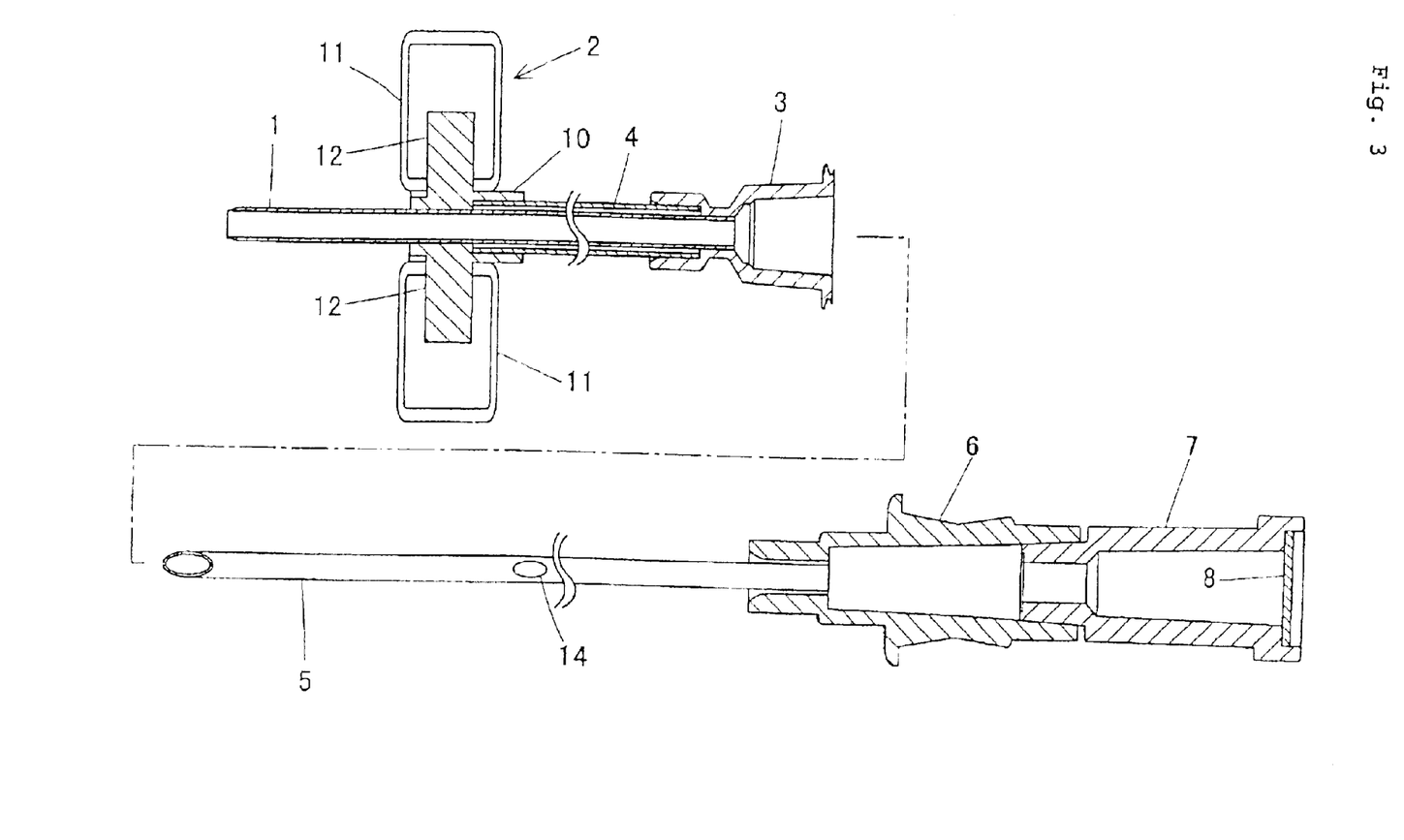
FIG. 3 is an exploded view of the indwelling needle disclosed in FIG. 2.

The first embodiment of the indwelling needle of the present invention is described below by referring to the drawings in FIGS. 1 to 5. FIGS. 1 to 3 show a winged indwelling needle. The indwelling needle comprises a cover needle 1, a fixing wing 2, a cover needle hub 3, a protecting tube 4, an inner needle (hollow needle) 5, an inner needle hub 6, a filter installing member 7, and a filter 8. Incidentally, the indwelling needle of the present invention also includes a catheter.

The cover needle 1 is an elongated transparent or translucent tube and has flexibility. The cover needle 1 is integrally formed of a plastic (resin) material, for example, a thermoplastic resin such as ethylene-tetrafluoroethylene copolymer (ETFE), tetrafluoroethylene-perfluoroalkyl ether copolymer (PFA), polypropylene resin, polyethylene resin, polyvinyl chloride resin, acrylonitrile-butadiene-styrene copolymer, polycarbonate resin, polyamide resin, and polyoxymethylene resin.

Figure 4:
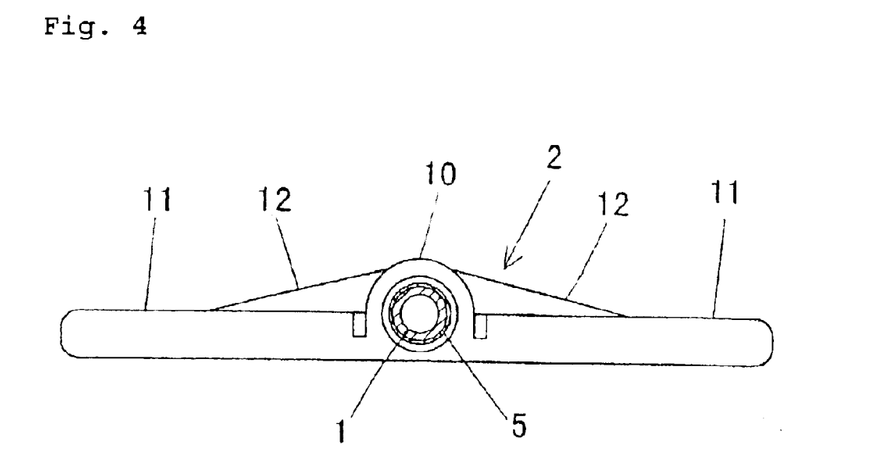
FIG. 4 is a sectional view taken in the direction of the arrows along line A—A of the indwelling needle disclosed in FIG. 2.
Figure 5:
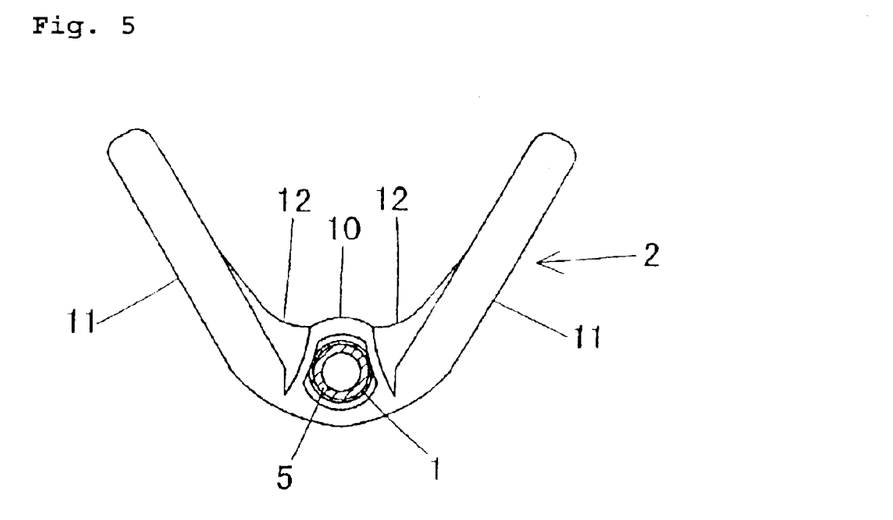
FIG. 5 is an operational view of the indwelling needle disclosed in FIG. 4.

As shown in FIGS. 4 and 5, the fixing wing 2 is mounted on a distal end side of the cover needle 1 and can be fixed on a skin of a patient. The fixing wing 2 comprises a holding tube 10 externally fitted and fixed on a distal end of the cover needle 1, a pair of wing parts 11 projecting from a lower portion of the holding tube 10 to the right and left sides, and a pair of connecting portions 12 mounted on the wing parts 11 and the holding tube 10. The fixing wing 2 is integrally formed of a plastic material and has flexibility. As the plastic material constituting the fixing wing 2, the same materials as those of the cover needle 1 are used.

Each of the connecting portions 12 connects a portion of the holding tube 10, which extends from a side surface of the holding tube 10 to an upper surface of the holding tube 10, and an upper surface of a wing part 11, which extends from an inside end portion to an outside end portion of each wing part 11. The connecting portions 12 form a fixing means with the holding tube 10 and both of the wing parts 11. When both of the wing parts 11 of the fixing wing 2 are picked up and brought relatively close to each other, the holding tube 10 and the cover needle 1 are diametrically pressed inwards via both of the connecting portions 12 and an inner portion of the holding tube 10 narrows. As a result, the fixing means fixes the cover needle 1 and the inner needle 5.

The cover needle hub 3 has a tubular shape and a distal end that is externally fitted and fixed on a proximal end of the cover needle 1. The cover needle hub 3 is integrally formed of a plastic material which is the same as those of the cover needle 1.

The protecting tube 4 constitutes a kink preventing means for preventing kink of the cover needle 1, has flexibility and is externally fitted on the cover needle 1. A distal end of the protecting tube 4 is inserted and fixed in a proximal end of the holding tube 10 and a proximal end of the protecting tube 4 is inserted and fixed in a distal end of the cover needle hub 3. The protecting tube 4 is integrally formed of a plastic material which is the same as those of the cover needle 1.

The inner needle 5 is removably inserted through the cover needle 1 and the cover needle hub 3, and the distal end of the inner needle 5 is projected forwards from the distal end of the cover needle 1. The inner needle 5 is an elongated tube having flexibility, the distal end of which is sharp. The inner needle 5 is integrally formed of, for example, stainless steel (SUS 304 is preferable).

The inner needle 5 has a side hole 14, in which flashback can be confirmed, on a side wall of the distal end of the inner needle 5. Flashback means that a blood flowing into the inner needle 5 on sticking the distal end of the inner needle 5 in a vein of a subject is confirmed. When the inner needle 5 is stuck in a blood vessel, under a skin or the like of a patient, a blood or a body fluid in the patient's blood vessel brings about flashback and flows out from the side hole 14 of the inner needle 5 to a space between the inner needle 5 and the cover needle 1. The sticking can easily be identified by visual observation of the blood or the body fluid in the space through the cover needle 1.

The inner needle hub 6 has a tubular shape, a distal end of which is externally fitted and fixed on a proximal end of the inner needle 5 and detachably inserted into a proximal end of the cover needle hub 3. The inner needle hub 6 is integrally formed of a plastic material which is the same as those of the cover needle 1.

The filter installing member 7 has a tubular shape, a distal end of which is detachably inserted into a proximal end of the inner needle hub 6. The filter installing member 7 is integrally formed of a plastic material which is the same as those of the cover needle 1. The filter 8 is installed in a proximal end of the filter installing member 7.

When infusion, blood collection or the like is performed, the inner needle 5 and the cover needle 1 of the indwelling needle of the present invention are stuck in a patient's blood vessel or the like. At this time, as shown in FIG. 5, both of the wing parts 11 of the fixing wing 2 are picked up to bring both of the wing parts 11 relatively close to each other. According to this procedure, the holding tube 10 and the cover needle 1 are pressed diametrically inwards via both of the connecting portions 12 to narrow the inner portion of the holding tube 10 and to fix the cover needle 1 and the inner needle 5 together. Since the cover needle 1 and the inner needle 5 are stuck in the patient's blood vessel or the like in the state that axial movement of the inner needle 5 is prevented by being fixed to the cover needle 1, the sticking procedure of the cover needle 1 and the inner needle 5 is easily and accurately performed.

In sticking of the cover needle 1 and the inner needle 5, the proximal end portion of the inner needle hub 6 is kept closed by the filter installing member 7 and the filter 8. Therefore, there is no fear of invading of various bacteria from the proximal end portion of the inner needle hub 6.

After the inner needle 5 and the cover needle 1 are stuck in the patient's blood vessel or the like, the fixing of the cover needle 1 and the inner needle 5 by the fixing wing 2 is released and each wing part 11 of the fixing wing 2 is fixed on the back of the patient's hand with a tape or the like. Then, the inner needle 5 is drawn out from the cover needle 1 and the cover needle hub 3. Additionally, an infusion tube or the like is connected with the cover needle hub 3 and infusion, blood collection or the like is performed with proper curving of the cover needle 1 and fixing of the cover needle on the back of the hand with a tape or the like.

In this case, since the cover needle 1 and the protecting tube 4 have flexibility, the cover needle 1 can be easily curved. Further, since the protecting tube 4 for preventing kink of the cover needle 1 is externally fitted on the cover needle 1, the kink of the cover needle 1 can be prevented in curving the cover needle 1. Accordingly, the procedure of curving the cover needle 1 to fix it on the patient's arm or the like with a tape or the like can be practiced easily, which results in easy and satisfactory performing of infusion, blood collection or the like.

Moreover, since the cover needle 1 is made of plastic, there is no fear of damaging a blood vessel or the like with an edge of the cover needle 1 during indwelling of the cover needle 1 in a blood vessel or the like. There is no problem about administration of a liquid medicine over a long period of time and indwelling of the cover needle 1 in a blood vessel or the like over a long period of time. In addition, the indwelling needle of the present invention is simple in structure and can be manufactured at low cost.

Figure 6:
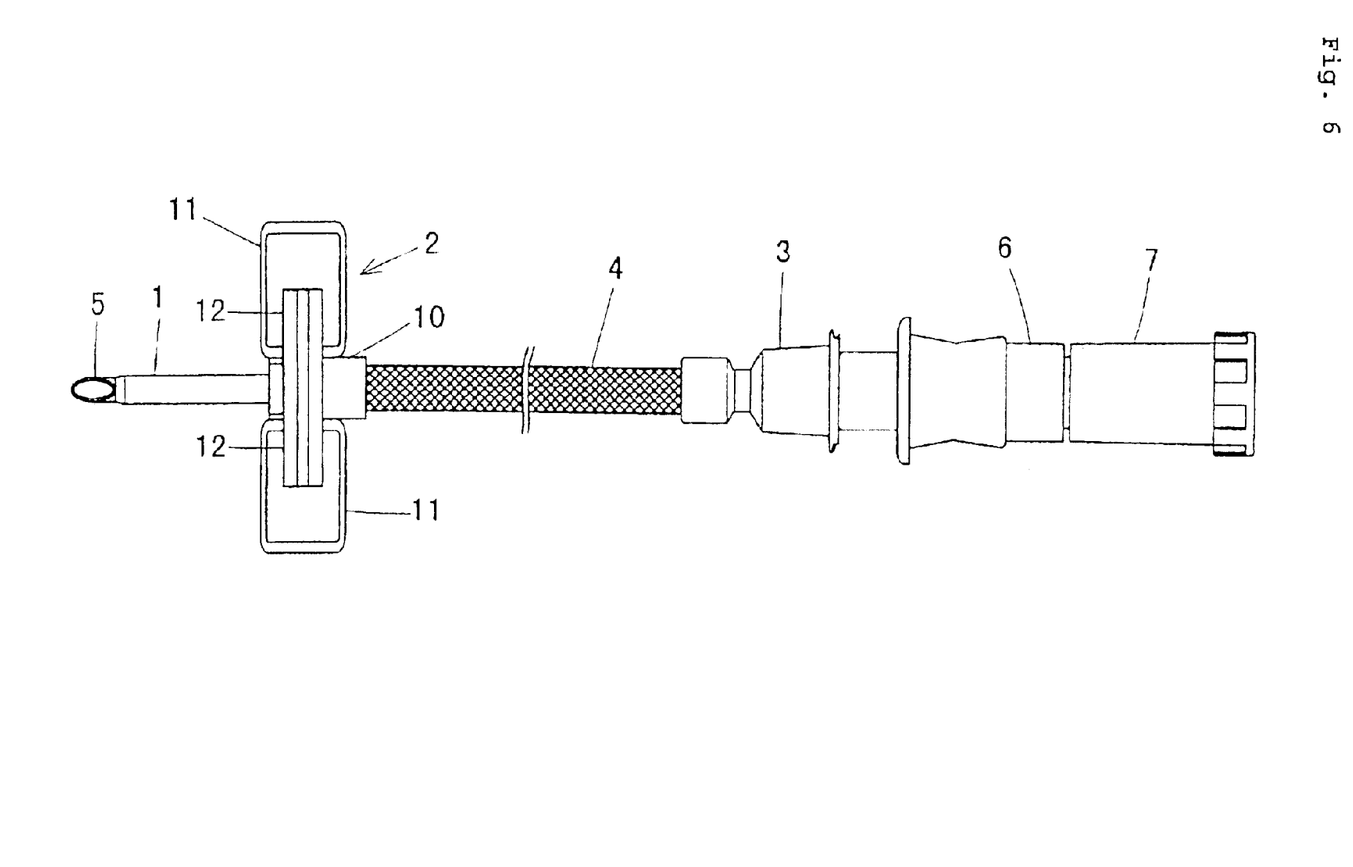
FIG. 6 is a plane view showing a second embodiment of the indwelling needle of the present invention.

The protecting tube 4 may be a mesh tube as shown in FIG. 6 which shows a second embodiment of the indwelling needle of the present invention.

Figure 7:
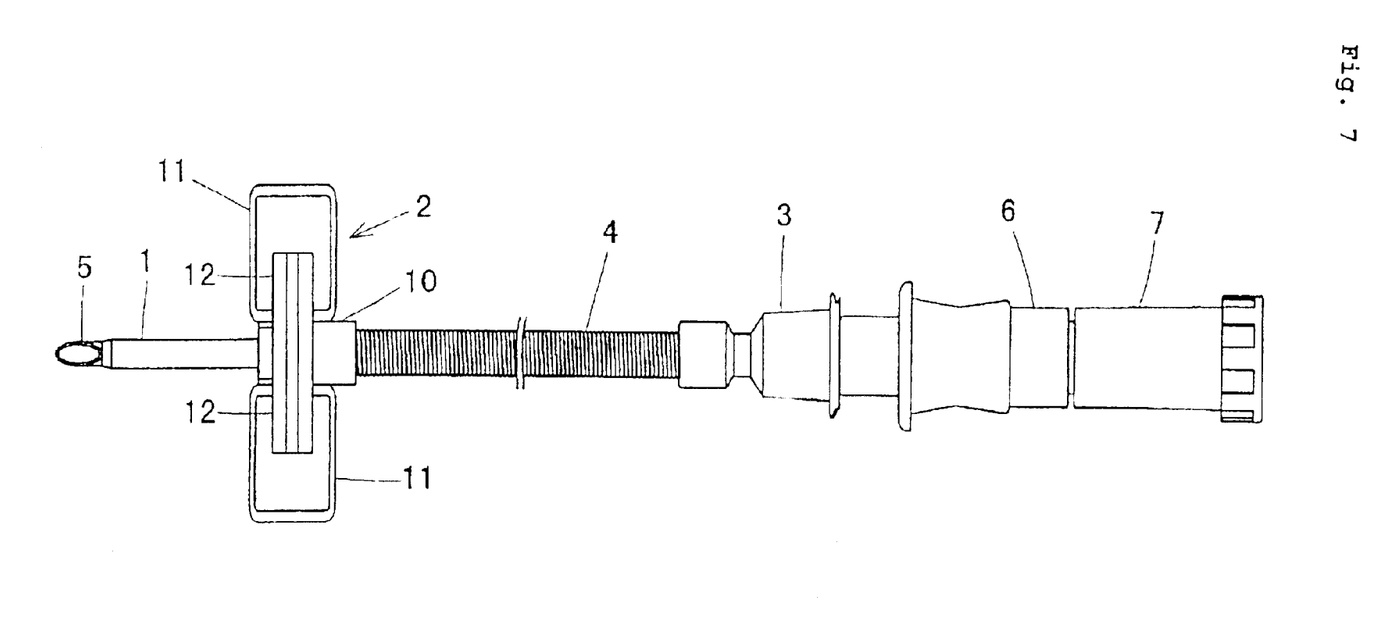
FIG. 7 is a plane view showing a third embodiment of the indwelling needle of the present invention.

The protecting tube 4 may be a coiled tube as shown in FIG. 7 which shows a third embodiment of the indwelling needle of the present invention. This coiled tube is manufactured by tightly and helically winding a synthetic fiber or a metallic yarn or sheet and heat-treating the same.

Figure 8:
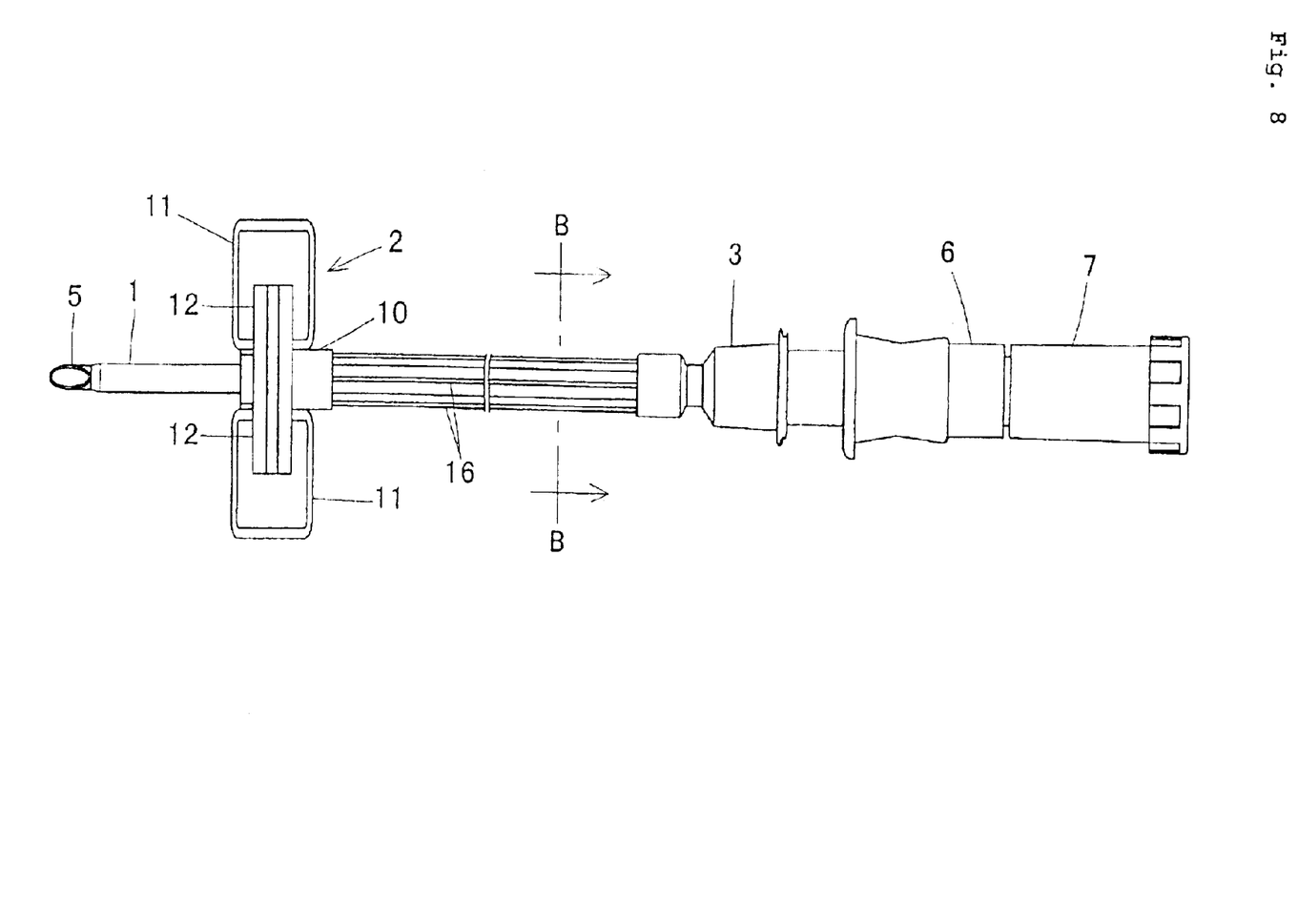
FIG. 8 is a plane view showing a fourth embodiment of the indwelling needle of the present invention.
Figure 9:
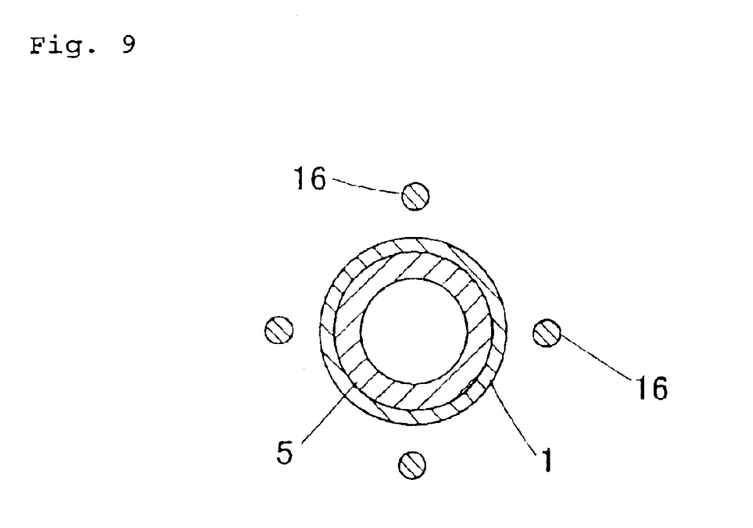
FIG. 9 is a sectional view taken in the direction of the arrows along line B—B of the indwelling needle disclosed in FIG. 8.

As the kink preventing means shown in FIGS. 8 and 9, a plurality of protecting members 16 made of metal or a synthetic fiber may be mounted around the cover needle 1 and spaced apart from each other. The protecting members 16 may be circumferentially mounted either at nearly equal intervals or at unequal intervals. The distal ends of the protecting members 16 are inserted and fixed in the proximal end of the holding tube 10 of the fixing wing 2 and the proximal ends of the protecting members 16 are inserted and fixed in the distal end of the cover needle hub 3. In the embodiment shown in FIGS. 8 and 9, four protecting members are shown. However, it is understood that three or more than four protecting members could be used.

Figure 10:
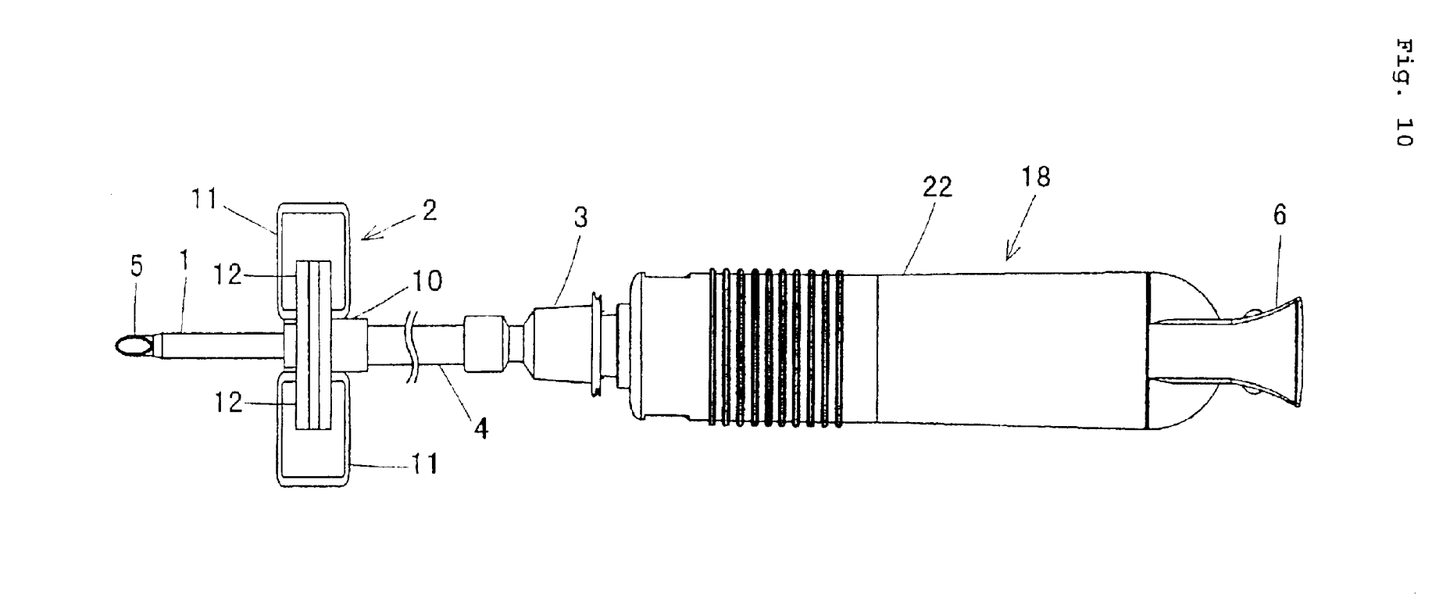
FIG. 10 is a plane view showing a fifth embodiment of the indwelling needle of the present invention.
Figure 11:
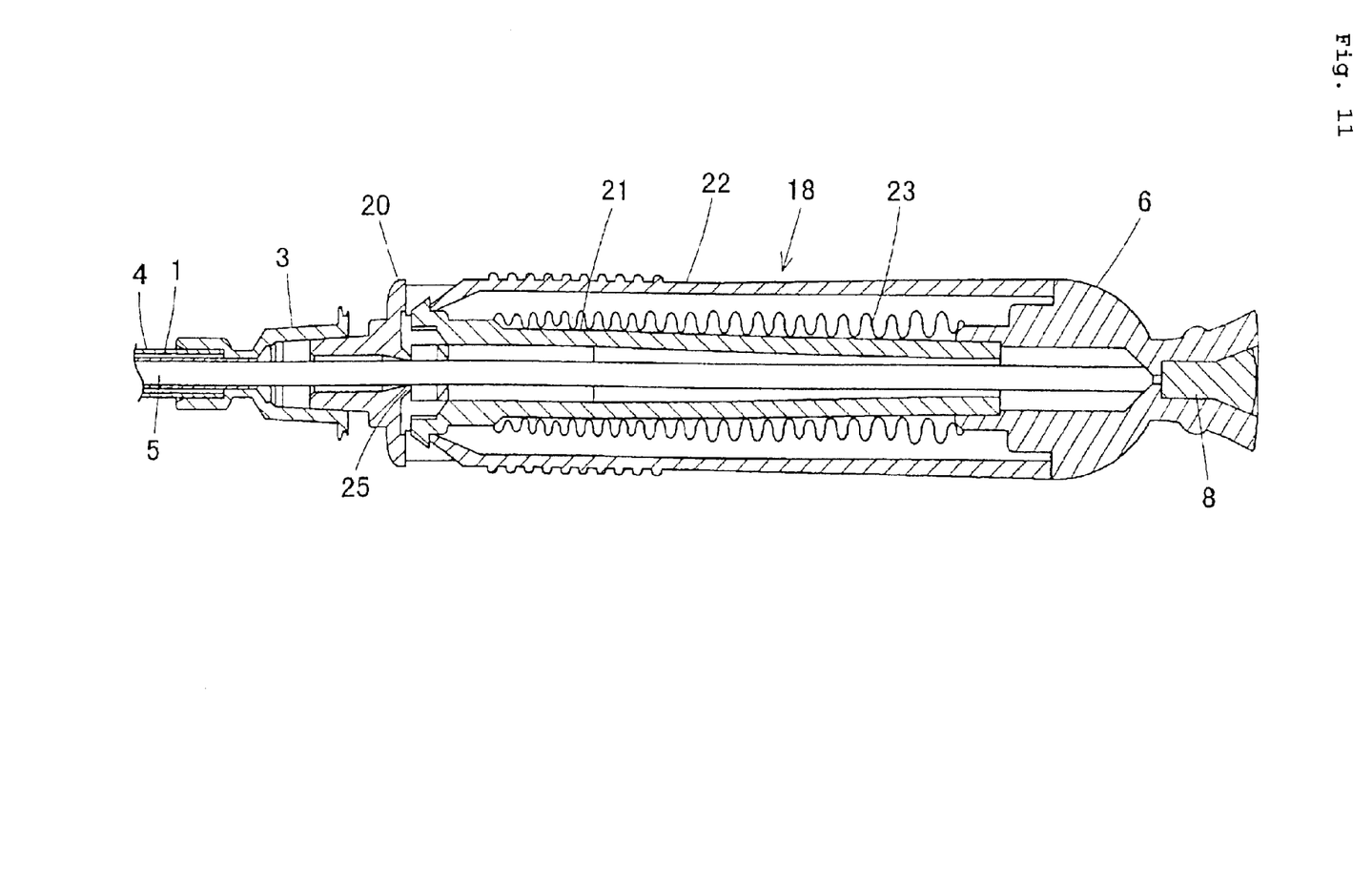
FIG. 11 is a sectional view of essential parts of the indwelling needle disclosed in FIG. 10.
Figure 12:
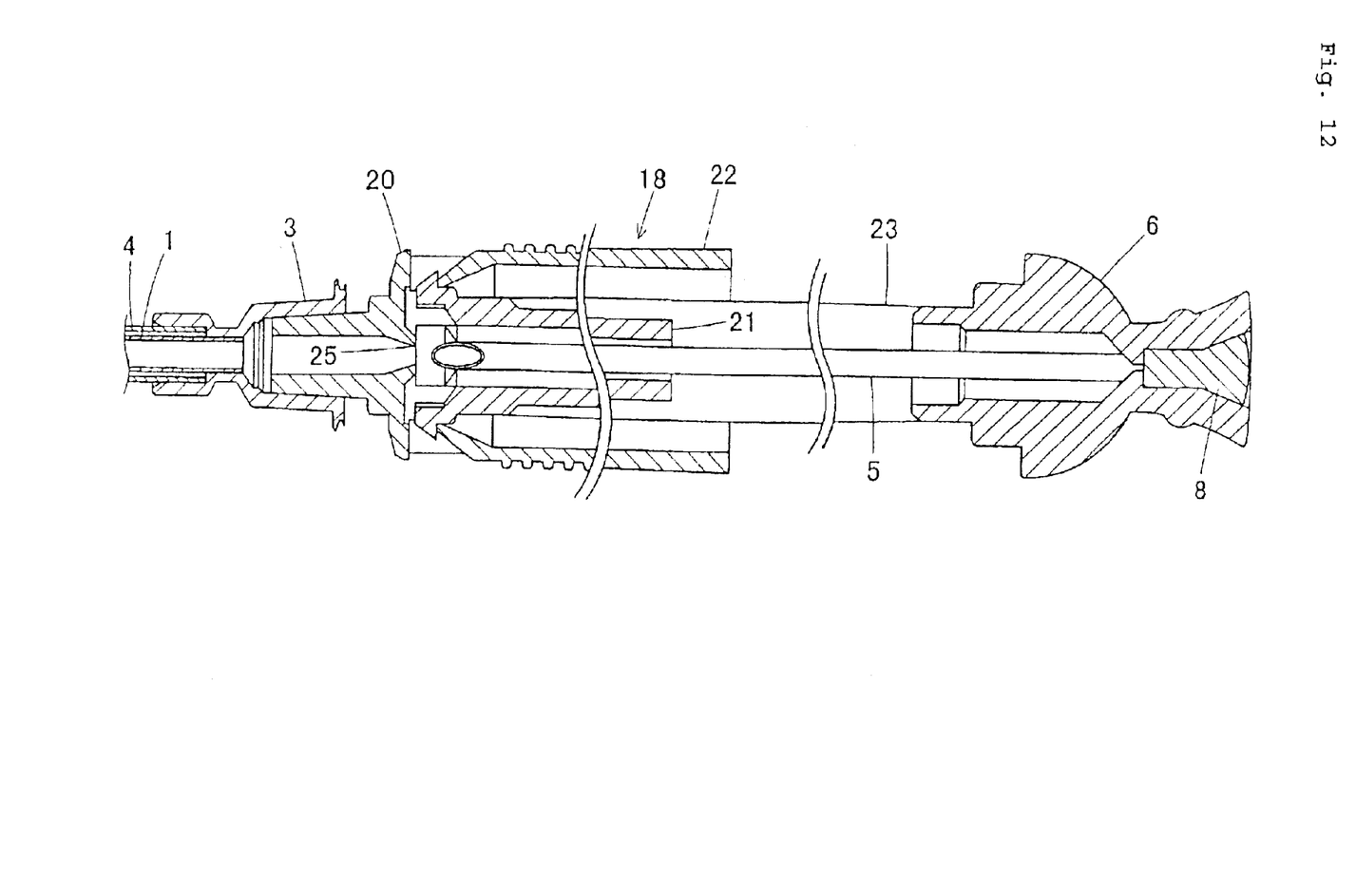
FIG. 12 is an operational view of the indwelling needle disclosed in FIG. 11.

As shown in FIGS. 10 to 12, which show a fourth embodiment of the indwelling needle of the present invention, the proximal end portion of the inner needle hub 6 may be closed with the filter 8 and an inner needle housing 18 may be interposed between the cover needle hub 3 and the inner needle hub 6. The inner needle housing 18 comprises a cylindrical insert member 20, an inner tube 21, an outer tube 22, a sleeve 23 and the like. The inner needle housing 18 can house the inner needle 5 when the inner needle 5 is drawn out from a patient's blood vessel or the like in order to prevent sticking accidents caused with the inner needle 5 by medical staff.

A distal end portion of the insert member 20 is detachably inserted into the proximal end of the cover needle hub 3 and the inner needle 5 is detachably inserted inside of the insert member 20. At an inner periphery of a proximal end portion of the insert member 20, a pressing portion 25 may be provided. When the inner needle 5 is inserted through the pressing portion 25 of the insert member 20, the pressing portion 25 can be resiliently deformed diametrically outwards and pressed against an outer surface of the inner needle 5 in a state that the inner needle 5 is slidable against the pressing portion 25. After the inner needle 5 is drawn out backwards from the pressing portion 25 of the insert member 20, the pressing portion 25 is deformed diametrically inwards by its own resilient force and the inner diameter of the pressing portion 25 becomes smaller than the outer diameter of the inner needle 5.

The inner tube 21 projects backwards from the proximal end portion of the insert member 20 and the inner needle 5 is inserted inside of the inner tube 21 movably in an axial direction. The distal end of the inner needle hub 6 is externally fitted and detachably fixed on a proximal end portion of the inner tube 21.

The outer tube 22 is externally fitted on the inner tube 21. The distal end of the outer tube 22 is fixed with the inner tube 21 and the proximal end of the outer tube 22 is fixed on the distal end of the inner needle hub 6.

The sleeve 23 is made of a plastic sheet having flexibility. The sleeve 23 is externally fitted on the inner tube 21, and the distal end of the sleeve 23 is externally fitted and fixed on an outer surface of a distal end of the inner tube 21 and the proximal end of the sleeve 23 is externally fitted and fixed on an outer surface of a distal end of the inner needle hub. The sleeve 23 is housed between the inner tube 21 and the outer tube 22 in an axially folded state. When the inner needle 5 is drawn out from the cover needle 1 and the cover needle hub 3, the sleeve 23 is axially extended to cover a portion on a more proximal side, than the inner tube 21, of the inner needle 5.

According to the indwelling needle shown in FIGS. 10 and 11, when the inner needle 5 and the cover needle 1 of the indwelling needle are stuck in the patient's blood vessel or the like, the distal end of the inner needle hub 6 is externally fitted and fixed on the proximal end of the inner tube 21 of the inner needle housing 18, the proximal end of the outer tube 22 is externally fitted on the distal end of the inner needle hub 6 and the sleeve 23 is kept housed between the inner tube 21 and the outer tube 22.

When the inner needle 5 is drawn out from the patient's blood vessel or the like, as shown in FIG. 12, the inner needle 5 is drawn out from the cover needle 1 and the cover needle hub 3 and the sleeve 23 is extended axially backwards to house the whole inner needle 5 in the inner tube 21 and the sleeve 23. After the inner needle 5 is drawn out from the cover needle hub 3, the pressing portion 25 is deformed diametrically inwards by its own resilient force and the inner diameter of the pressing portion 25 becomes smaller than the outer diameter of the inner needle 5 to prevent the inner needle 5 from being re-inserted into the cover needle hub 3.

After the inner needle 5 is drawn out from the cover needle 1 and the cover needle hub 3, the whole inner needle 5 is covered with the inner tube 21 and the sleeve 23 to be housed therein. Since the inner needle 5 housed in the inner tube 21 and the sleeve 23 is prevented from being re-inserted into the cover needle side hub 3, sticking accidents caused with the inner needle 5 by medical staff can be well prevented.

In the foregoing examples, the kink preventing member is constructed out of the protecting tube or the linear protecting members. However, a protecting member made of a rectangular sheet may be used instead of the linear protecting members. Or, the kink preventing means may be constructed out of a coiled spring or the like. Further, the cover needle itself may be a reinforced needle to construct the kink preventing means. Still further, a combination of any of the kink preventing means described above is also available.

EFFECT OF THE INVENTION

According to the indwelling needle of the present invention, the cover needle is, though made of plastics, not kinked in infusion or the like when it is curved. Accordingly, a procedure of curving the cover needle to fix it on a patient's arm or the like with a tape or the like is easily practiced and infusion or blood collection from a peripheral vein in a back of a hand or the like is easily and satisfactorily performed. Moreover, the structure of the indwelling needle of the present invention is simple, and the manufacture can be carried out at low cost.

Additionally, in the indwelling needle of the present invention, the inner needle and the outer needle can be fixed with the fixing means so that the sticking of the inner needle and the cover needle in a patient's blood vessel or the like can be easily and accurately performed. Since the structure of the fixing means is simple, the indwelling needle can be manufactured at low cost.

The indwelling needle of the present invention can prevent sticking accidents caused with the inner needle by medical staff when the inner needle is drawn out from the cover needle and the cover needle hub. Since the indwelling needle of the present invention can also prevent the inner needle from being reinserted into the cover needle and the cover needle hub, sticking accidents caused with the inner needle by medical staff are more satisfactorily prevented.

What is claimed is:

1. An indwelling needle comprising
   a) a flexible and elongated cover needle made of plastic tubing,
   b) a fixing wing externally fitted and fixed on a distal end of the cover needle,
   c) a cover needle hub mounted on a proximal end of the cover needle,
   d) an inner needle which is detachably situated in the cover needle and the cover needle hub and the distal end of which projects forwards from the cover needle, and
   e) a protecting tube for preventing kink of a portion of the cover needle and which is externally fitted on the cover needle between the fixing wing and the cover needle hub.

2. The indwelling needle according to claim 1, wherein the fixing wing has a fixing means for releasably fixing the cover needle and the inner needle.

3. The indwelling needle according to claim 2, wherein the fixing wing comprises a holding tube externally fitted and fixed on the cover needle, a pair of wings projecting outwardly from the holding tube to right and left sides, and a pair of connecting portions connecting an upper surface or a lower surface of each wing and the holding tube.

4. The indwelling needle according to claim 1, wherein an inner needle hub is mounted on a proximal end of the inner needle, an inner needle housing is interposed between a proximal end of the cover needle hub and the inner needle hub, and the inner needle housing comprises
   a) an inner tube in which the inner needle is inserted,
   b) an outer tube which is externally fitted on the inner tube, and
   c) a sleeve which is externally fitted on the inner tube, a distal end of which is fixed on the inner needle housing, a proximal end of which is externally fitted and fixed on a distal end of the inner needle hub, and which is housed between the inner tube and the outer tube in an axially folded state and is capable of being axially extended when the inner needle is removed from the cover needle and the cover needle hub so as to cover a portion of the inner needle which is situated on a proximal side of the inner tube.

5. The indwelling needle according to claim 4, wherein the inner needle housing includes a flexible pressing portion biased against an outer surface of the inner needle when the inner needle is situated in the cover needle and the cover needle hub and is capable of deforming diametrically inwards by its own resilient force to have an inner diameter which is smaller than an outer diameter of the inner needle when the inner needle is drawn out backwards from the pressing portion and removed from the cover needle and the cover needle hub.

* * * * *